United States Patent [19]

Huber

[11] Patent Number: 4,530,795
[45] Date of Patent: Jul. 23, 1985

[54] PROCESS FOR PREPARATION OF 16 α-METHYL CORTICOIDS FROM Δ¹⁶-STEROIDS

[75] Inventor: Joel E. Huber, Texas Township, Kalamazoo County, Mich.

[73] Assignee: The Upjohn Company, Kalamazoo, Mich.

[21] Appl. No.: 584,278

[22] Filed: Feb. 27, 1984

[51] Int. Cl.³ ............................................. C07J 7/00
[52] U.S. Cl. .............................. 260/397.4; 260/397.45
[58] Field of Search ......................... 260/397.4, 397.45

[56] References Cited

U.S. PATENT DOCUMENTS 4,041,055  8/1977  Phephard et al. ................. 260/397.3
4,216,159  8/1980  Hessler et al. ....................... 260/397

OTHER PUBLICATIONS

VanRheenen, et al., "New Synthesis of Corticosteroids from 17-Keto Steroids: Application and Stereochemical Study of the Unsaturated Sulfoxide-Sulfenate Rearrangement", J. Org. Chem., Communications, vol. 44, No. 9, pp. 1582–1584, (1979).
Redpath, et al., "Stereoselective Synthesis of Steroid Side-Chains", Chemical Society Reviews, vol. 12, No. 1, pp. 75–98, (1983).
Morera, et al., "Preparative and Stereochemical Features of the Sulfoxide-Sulfenate [2,3]Sigmatropic Rearrangement in 17-Vinyl-17-Hydroxy Steroids", J. of Org. Chem., vol. 48, No. 1, pp. 119–121, (1983).
Daniewski, et al., "Synthesis of the Corticoid Side-Chain", J. of Org. Chem., vol. 47, No. 15, pp. 2993–2995, (1982).
Barton, et al., "Efficient Synthesis of the Corticosteroid Side-Chain from 17-Ketones", J. of the Chem. Soc. Chemical Communications, No. 15, pp. 774–775, 1981.
"Steroids", Kirt-Othmer Encyclopedia of Chemical Technology, 2nd Edition, vol. 18, Interscience Publishers, Division of John Wiley and Sons, Inc., (1969), pp. 840–843.
Douglass, et al., "A Superior Method for Preparing Sulfinyl Chlorides", J. Org. Chem., vol. 33, pp. 2104–2106, (1968).
Evans, et al., "Allylic Sulfoxides: Useful Intermediates in Organic Synthesis", Accounts of Chemical Research, vol. 7, 147–155, (1974).
Djerassi, Steroid Reactions an Outline for Organic Chemists, Chapter 1, by Keana, pp. 1–87, Holden-Day, Inc., San Francisco, (1963).

*Primary Examiner*—Elbert L. Roberts
*Attorney, Agent, or Firm*—Joan Thierstein; Bruce Stein

[57] ABSTRACT

This invention discloses a general process for the production of corticoids from respective steroid-type compounds having a double bond from C-16 to C-17. The invention provides a viable alternative synthesis of 17α-hydroxy-progesterones and like corticoids.

9 Claims, No Drawings

PROCESS FOR PREPARATION OF 16 α-METHYL CORTICOIDS FROM Δ$^{16}$-STEROIDS

BACKGROUND OF THE INVENTION

The corticoids are a particular type of steroid having the basic carbon skeletal formula I which contains 21 carbon atoms in 4 rings, A thru D.

The A–D rings of the steroid nucleus being relatively planar will have some groups which are positioned above (β) the plane of cyclopentenophenanthrene nucleus and are designated by ▬ and others which are positioned below (α) the plane and are designated by ----. Further, ~ indicates the substituent is either positioned in the α or in the β position to the plane of the ring.

A well known example of the corticoids is dexamethasone, a glucocorticoid which is represented by the formula II.

The pharmaceutical utility of the corticoids is well known to those skilled in the art. They are used for relief of inflammatory manifestations, endocrine disorders, adrenocortical insufficiency, rheumatic disorders, dermatologic diseases, allergic states, ophthalmic diseases, respiratory diseases, hematologic disorders, neoplastic diseases, edematous states, etc.

The corticoids are administered orally, topically or parenterally in dosages which are well known to those skilled in the art.

A preparation of corticoid-type compounds of the similar scope as the present invention is disclosed in U.S. Pat. No. 4,041,055. The preparation makes use of a sulfenate-sulfoxide rearrangement to define the stereochemistry of corticosteroids at C-17. The rearrangement is also discussed by VanRheenen, et al., in the "New Synthesis of Corticosteroids from 17-Keto Steroids: Application and Stereochemical Study of the Unsaturated Sulfoxide-Sulfenate Rearrangement," *J. Org. Chem., Communications*, vol. 44, no. 9, pp. 1582–4 (1979). More recently each of the following references discusses processes related to the corticoid groups at the 17 position of the steroidal ring: Redpath, et al., "Stereoselective Synthesis of Steroid Side-Chains", *Chemical Society Reviews*, vol. 12, no. 1, pp. 75–98 (1983); Morera, et al., "Preparative and Stereochemical Features of the Sulfoxide-Sulfenate [2,3] Sigmatropic Rearrangement in 17-Vinyl-17-Hydroxy Steroids", *J. of Org. Chem.*, vol. 48, no. 1, pp. 119–21 (1983); Daniewski, et al. "Synthesis of the Corticoid Side-Chain", *J. of Org. Chem.*, vol. 47, no. 15, pp. 2993–5 (1982); and Barton, et al., "Efficient Synthesis of the Corticosteroid Side-Chain from 17-Ketones", *J. of the Chem. Soc. Chemical Communications*, no. 15, pp. 774–5, 1981. However, none of the above teachings appreciates the preparation of 17-α-hydroxyprogesterones of the present invention from steroidal-type compounds having a double bond from the 16 to 17 carbon in the D ring. The invention includes selected desireable variations of double bonds and substituents on rings A–C.

SUMMARY OF THE INVENTION

The present process comprises the preparation of corticoids having substituents on ring D as shown by formula X where $R_{21}$ is as defined below; wherein the improvement comprises (1) contacting a compound having a ring D as shown by formula XI where $R_{21}$ is as defined below with methylmagnesium halide in the presence of a copper catalyst; (2) treating the compound of step (1) with aryl sulfinyl halide or mixed anhydride comprising an enol sulfinate; and (3) adding a thiophile to the reaction mixture of step (2) to obtain the corticoid having the substituents on ring D as shown by formula X.

The present invention is more particularly a process for the preparation of a compound having the formula IV (see Scheme A) wherein ▬▬▬ is optionally a single or double bond with the proviso that when one of ▬▬▬ or ▬▬▬ is a double bond the other cannot be a double bond;

$R_3$ is an (O), (H, α-OR) or (H, β-OR) wherein R is hydrogen or a protecting group;

$R_6$ is hydrogen, methyl or fluoro;

$R_9$ is hydrogen, fluoro, chloro or bromo;

$R_{11}$ is (H), (H,H), (H, β-chloro), (O), (H, α-OR') or (H, β-OR'), wherein R' is hydrogen, a protecting group;

$R_{21}$ is hydrogen, halogen or OR" wherein R" is hydrogen or a protecting group;

which comprises (1) contacting a compound of formula III wherein ▬▬▬, ▬▬▬, ▬▬▬, $R_3$, $R_6$, $R_9$, $R_{11}$ and $R_{21}$ are as defined above; with methyl magnesium halide in the presence of a copper catalyst;

(2) treating the compound of step (1) with aryl sulfinyl halide or mixed anhydrides to prepare an enol sulfinate III$_2$;

(3) adding a thiophile to the reaction mixture of step (2); to obtain the compound having formula IV.

The compound of formula III is well known in the art or can be prepared by methods known in the art. For example processes developed from 1939–51, beginning with Marker's degradation of sapogenin and processes patterned thereafter give compounds of formula III. The degradation processes all begin with C-27 cholestane derivatives obtained from natural sources. Another process involving an acid catalyzed deamination of an N-nitroso derivative also from C-27 cholestane derivatives readily gives a compound of the formula III for use in the present process. See "Steroids", *Kirk-Othmer Encyclopedia of Chemical Technology*, 2nd edition, vol. 18, Interscience Publishers, a division of John Wiley and Sons, Inc. (1969), particularly pp. 840–3. U.S. Pat. No. 4,216,159 discloses a process for the preparation of a compound III having the formula IIIa, IIIb, IIIc or IIId wherein $R_6$, $R_{11}$ and $R_{21}$ are as defined above, or the equivalent thereof.

Additionally, other preparations for various 16-unsaturated steroids are disclosed in U.S. Pat. No. 4,216,159 which may be within the definition of the compound having formula III of the present invention.

Halide means bromo, chloro and iodo.

The copper catalyst may be cuprous iodide, cuprous bromidedimethyl sulfide complex or cuprous cyanide and the like.

Step 2 comprises adding a sulfinyl radical source which may be an aryl sulfinyl halide or a mixed anhydride.

Aryl means phenyl, p-tolyl, p-nitrophenyl, p-, m-, or o-methoxy phenyl and the like. Aryl sulfinyl halides may be prepared according to the procedures by Douglass, et al., "A Superior Method for Preparing Sulfinyl Chlorides", *J. Org. Chem.*, vol. 33, pp. 2104–6 (1968)

Mixed anhydrides are prepared from p-toluene sulfinic acid or benzene sulfinic acid and the like which is commercially available, mixed with trifluoro or trichloro acetic anhydride under anhydrous conditions. The resulting mixed anhydride is old in the art. Such anhydrides may be prepared in situ. However, although the anhydrides may be unstable they can be made separately from the reaction mixture.

Thiophiles for use in this invention are described by Evans, et al. in "Allylic Sulfoxides: Useful Intermediates in Organic Synthesis", Accounts of Chemical Research, vol. 7, 147-55 (1974). The thiophiles preferred are sodium methyl xanthate and is sodium thiocyanate.

The protecting groups which may be required on the compounds in the invention process are those appropriate and are selected from among those well known by those of ordinary skill in the art. For example, see Djerassi, Steroid Reactions an Outline for Organic Chemists, chapter 1 by Keana, pp. 1-87, Holden-Day, Inc. San Francisco (1963).

Generally, the present process comprises adding the methylmagnesium halide; preferably a stoichiometric amount, to a solution of the compound of formula III and a copper catalyst. The solvent is an aprotic solvent such as 1,2-dimethoxyethane, diethyl ether or methylene chloride and preferably anhydrous tetrahydrofuran. The copper catalyst is cuprous iodide, cuprous bromide-dimethyl sulfide complex, or cupric acetate monohydrate, preferably cuprous acetate monohydrate. The preferred temperature of the addition reaction mixture may vary from +40° C. to −50° C. but preferably the temperature is maintained from −35° C. to −40° C. when preparing the compounds of the examples in the following material. After a determination that the methyl magnesium addition is complete, for example, by thin layer chromatography the reaction mixture is quenched by a sulfinyl radical source. The sulfinyl radical source is an aryl sulfinyl halide preferably phenylsulfinyl chloride but may also be a mixed anhydride prepared as set out above. As noted above the anhydride may be prepared in situ as well. Following the addition of the sulfinyl radical source the temperature of the reaction mixture may be allowed to rise to from −10° C. to 40° C. and for most compounds of this step rearrangement as shown in Scheme A of the formula III$_2$ and formula III$_3$ occurs at about room temperature. However, temperature and time are not critical but can be readily determined for the given rearrangement. Finally, the reaction mixture is cooled and the sulfenate ester intercepted by at least a slight excess over a stoichiometric amount of a thiophile. Such interception may be accomplished by either the addition of the thiophile to the reaction mixture or the addition of the reaction mixture to an excess of thiophile. The pH of the reaction is adjusted to yield the compound of formula IV. Again the temperature and reaction time is not critical although the preferred temperature is one of convenience and thus is the same as for the rearrangement described above. Likewise, the pH required for obtaining the compound having formula IV is readily determined. Isolation of the compound having formula IV from the reaction mixture is accomplished by conventional methods.

Although Scheme A shows each step (1) through (3) as separate steps the process of the invention can of course be carried out in a one pot process more adequately shown in Scheme B.

The following examples describe the preparation of compounds having the formula IV according to the invention process. The examples, therefore, are indicative of the embodiment of this invention but are not to be construed as limitative. Those skilled in the art will promptly recognize variations from the procedures both in the starting materials as well as reaction conditions and techniques of the invention process.

EXAMPLE I

17α-,21-Dihydroxy-16α-methylpregna-4,9(11)-diene-3,20-dione 21-acetate

A solution of 3.68 g of 21-hydroxy-pregna-4,9(11),16-triene-3,20-dione 21-acetate and 150 mg of cupric acetate monohydrate in 80 ml anhydrous tetrahydrofuran is cooled to −45° C. and 7.8 ml of a 2.03$\underline{M}$ methylmagnesium chloride solution in tetrahydrofuran is added dropwise over 20 minutes. The temperature is maintained in the −40° C. to −45° C. range during this addition. The reaction is checked by tlc (acid quench of a small sample) which shows that all of the starting material is reacted. The magnesium enolate is quenched with addition of 1.30 ml (1.09 equivalents) of freshly distilled phenylsulfinyl chloride. Then the temperature is allowed to slowly rise to 20° C. over 30 minutes. After one hour the reaction solution is cooled to 5° C. and a solution of 1.47 g of sodium methyl xanthate in 35 ml of methanol is added dropwise over 7 minutes. The solution is warmed to 20° C. and, after 30 minutes stirring, the pH is adjusted to 3.8 with dilute sulfuric acid and the reaction mixture is added to 100 ml of water. This is extracted with methylene chloride (100 ml and 2×50 ml) and each extract is washed sequentially with the same 150 ml portion of water. The combined extracts are concentrated on the rotovap and the resulting dark oil is dissolved in 35 ml of warm methanol. Solids form immediately and after standing at −15° C. overnight, the solids are collected by filtration and washed thoroughly with cold methanol. Air-drying of these solids to constant weight affords 2.83 g of 17α-,21-dihydroxy-16α-methylpregna-4,9(11)-diene-3,20-dione 21-acetate as a mono-methanol solvate; mp 197°–201° C.

EXAMPLE II

17α,21-Dihydroxy-16α-methylpregna-1,4,9(11)-triene-3,20-dione 21-acetate

A solution of 3.66 g of 21-hydroxy-pregna-1,4,9(11),16-tetraene-3,20-dione 21-acetate and 150 mg of cupric acetate monohydrate in 80 ml anhydrous tetrahydrofuran is cooled to −35° C. and 8.0 ml of 2$\underline{M}$ methylmagnesium chloride is added over 10 minutes at −35° C. to −37° C. After tlc indicates the conjugate Grignard reaction is complete, the magnesium enolate is quenched with 1.43 ml of phenylsulfinyl chloride. The solution is then warmed rapidly to 12° C. and after stirring for one hour at 12° C. to 20° C., a solution of 898 mg of sodium thiocyanate in 30 ml of methanol is added dropwise over 7 minutes. The resulting cloudy mixture is stirred at 20° C. for 30 minutes. Then, after adjusting the pH to 3.8 with 10% aqueous sulfuric acid, the reaction mixture is added to 150 ml water and extracted with methylene chloride as described above. The combined extracts are concentrated on the rotovap to provide 5.69 g of higher boiling material. This residue is chromatographed on a 170 g mplc column (0.043–0.060 mm silica gel). The column is developed with 5% acetone in methylene chloride and 25 ml fractions are collected. Concentration of those fractions containing the desired product provides 2.66 g of a residue which is crystallized from 20 ml of n-butyl chloride at −20° C.

The solids are collected by filtration, washed with cold n-butyl chloride and air-dried to constant weight to give 2.35 g of 17α-,21-dihydroxy-16α-methylpregna-1,4,9(11)-triene-3,20-dione 21-acetate; mp 202° C.–205° C.
FORMULAS
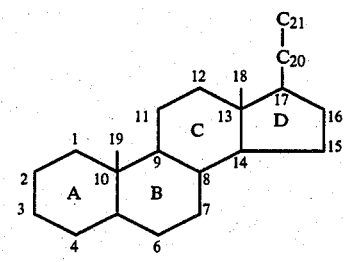 I
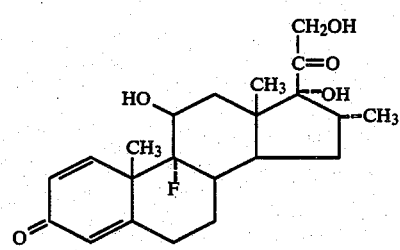 II
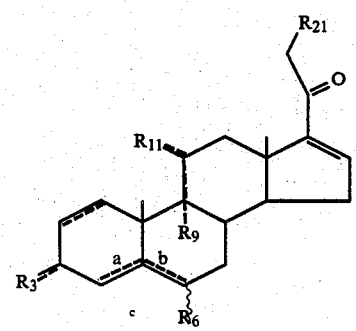 III
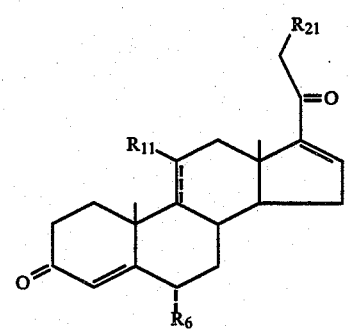 IIIa
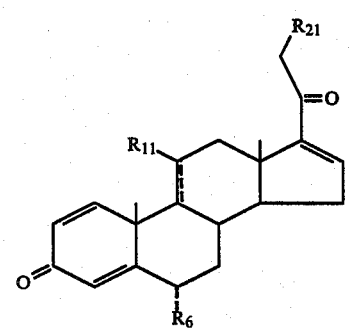 IIIb
-continued
FORMULAS
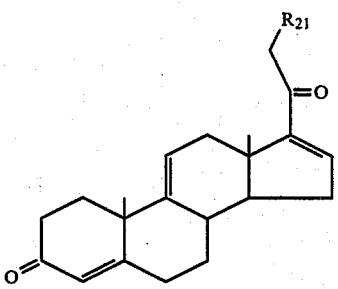 IIIc
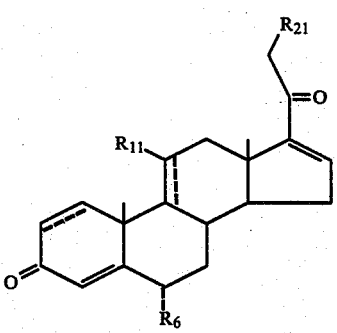 IIId
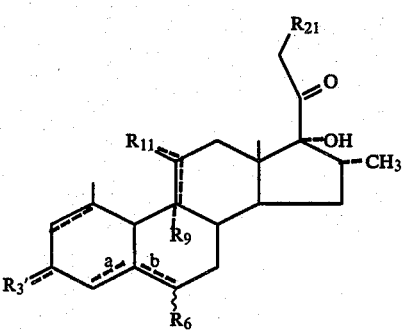 IV
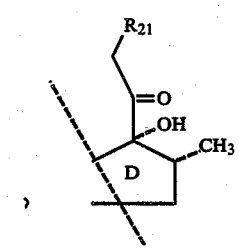 X
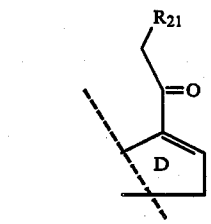 XI

SCHEME A
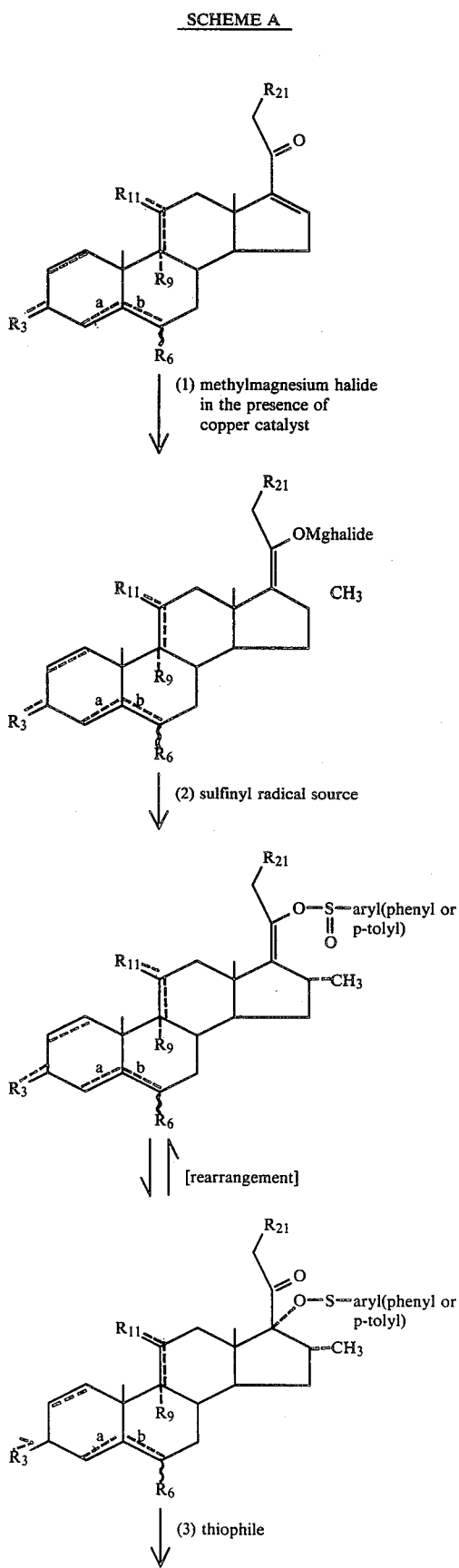
SCHEME B
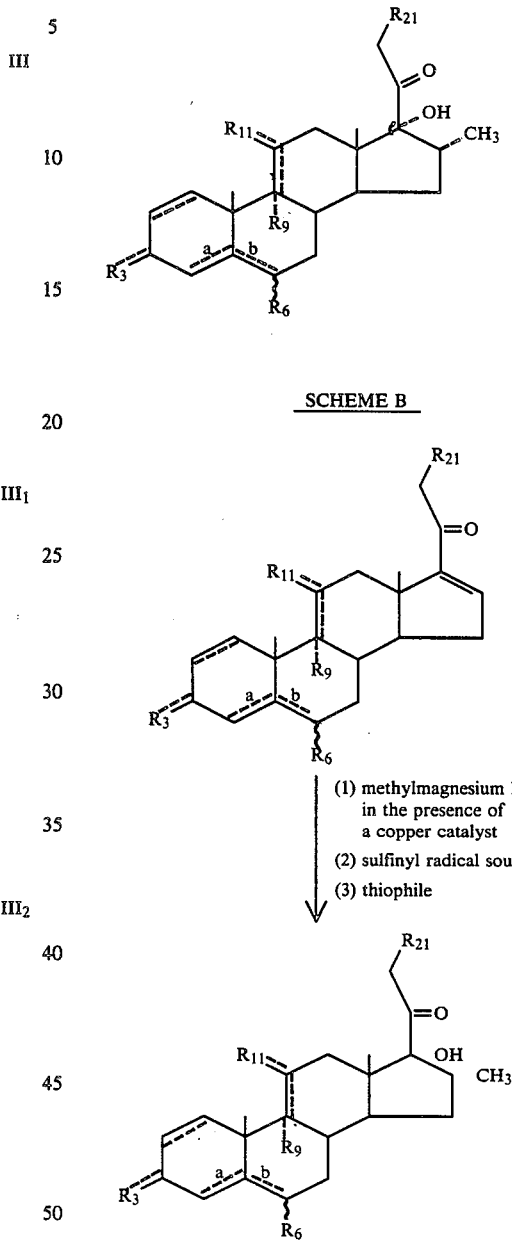
I claim:
1. In a process for the preparation of a corticoid having the ring D of formula
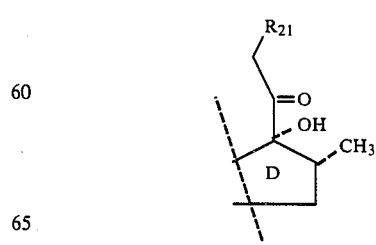
wherein $R_{21}$ is hydrogen, halogen or OR'' wherein R" is hydrogen or a protecting group and where the improvement comprises
(1) contacting a compound having the ring D of formula

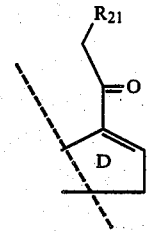

wherein $R_{21}$ is a defined above with methylmagnesium halide in the presence of a copper catalyst;
(2) treating the reaction mixture of step (1) with a sulfinyl halide or mixed anhydride comprising an enol sulfinate; and
(3) adding a thiophile to the reaction mixture of step (2) to obtain the corticoid.

2. A process for the preparation of a compound of the formula

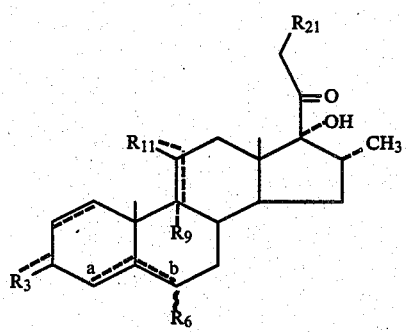

wherein ⎯ is optionally a single or double bond with the proviso that when one of ⎯ or ⎯ is a double bond the other cannot be a double bond;

$R_3$ is an (O), (H, $\alpha$-OR) or (H, $\beta$-OR) wherein R is hydrogen or a protecting group;

$R_6$ is hydrogen, methyl or fluoro;

$R_9$ is hydrogen, fluoro, chloro or bromo;

$R_{11}$ is (H), (H,H), (H, $\beta$-chloro), (O), (H, $\alpha$-OR') or (H, $\beta$-OR'), wherein R' is hydrogen or a protecting group;

$R_{21}$ is hydrogen, halogen or OR" wherein R" is hydrogen or a protecting group; which comprises:

(1) contacting a compound of formula

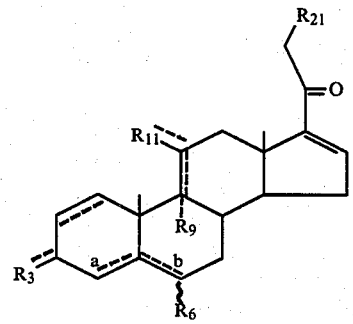

wherein , , $R_3$, $R_6$, $R_9$, $R_{11}$ and $R_{21}$ are as defined above with methylmagnesium halide in the presence of a copper catalyst;
(2) treating the reaction mixture of step (1) with aryl sulfinyl halide or mixed anhydrides to prepare an enol sulfinate;
(3) adding a thiophile to the reaction mixture of step (2); to obtain the compound having formula IV.

3. A claim according to claim 2 wherein $R_3$ is (O), $R_6$ is in the $\alpha$-position, ⎯⎯, is a double bond, ⎯⎯ is a single bond, $R_{11}$ is attached to the ring by a single bond and is a hydrogen, $\alpha$-OR' or $\beta$-OR' with the proviso that if $R_{11}$ is OR' then the ⎯⎯ in ring C is a single bond, and $R_{21}$ is OR".

4. A process according to claim 2 wherein the compound having formula IV prepared is 17$\alpha$-,21-dihydroxy-16$\alpha$-methylpregna-4,9(11)diene-3,20-dione 21-acetate.

5. A process according to claim 2 wherein the compound having formula IV prepared is 17$\alpha$-,21-dihydroxy-16$\alpha$-methylpregna-1,4,9(11)-triene-3,20-dione-21-acetate.

6. A process of claim 2 wherein the copper catalyst is cuprous iodide, cuprous bromide-dimethyl sulfide complex or cupric acetate monohydrate.

7. A process of claim 2 wherein the sulfinyl radical source is aryl-sulfinyl chloride or a mixed anhydride comprising the reaction product of p-toluene sulfinic acid or benzene sulfinic acid and trifluoro or trichloro acetic anhydride.

8. A process of claim 7 wherein the sulfinyl radical source is phenylsulfinyl chloride or p-tolylsulfinylchloride.

9. A process of claim 7 wherein the thiophile is sodium methyl xanthate or sodium thiocyanate.

* * * * *

UNITED STATES PATENT OFFICE
CERTIFICATE OF CORRECTION

Patent No. 4,530,795            Dated 23 July 1985

Inventor(s) Joel E. Huber

It is certified that error appears in the above-identified patent and that said Letters Patent are hereby corrected as shown below:

Column 2, line 10: "------- or -------" should read:-- ---a--- or ---b--- --.

Column 2, line 23: "-------, -------, -------," should read -- -------, ---a---, ---b---, --.

Column 2, line 34: "example processes" should read -- example, processes--.

Column 6, line 41: 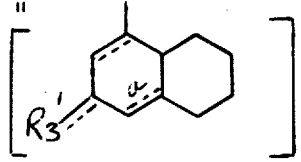 should read 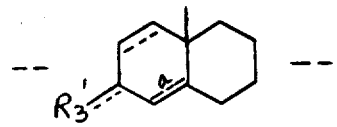

Column 7, line 27: 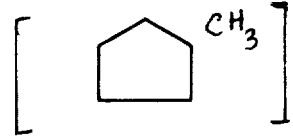 should read 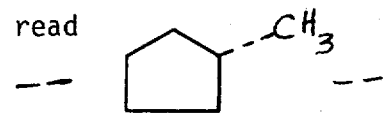

Column 7, line 63: 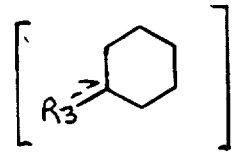 should read 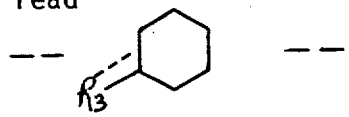

Column 8, line 45: 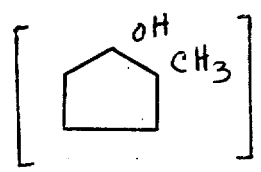 should read 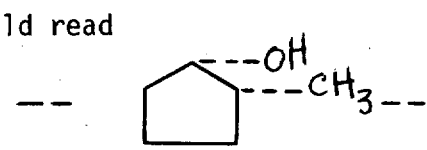

UNITED STATES PATENT OFFICE
CERTIFICATE OF CORRECTION

Patent No. 4,530,795            Dated 23 July 1985

Inventor(s) Joel E. Huber

It is certified that error appears in the above-identified patent and that said Letters Patent are hereby corrected as shown below:

Column 9 (Claim 2) lines 40, 41: "wherein _____ is optionally a single or double bond with the proviso that when one of _____ or _____ is a double" should read --wherein ------- is optionally a single or double bond with the proviso that when one of ---a--- or ---b--- is a double --.

Column 10 (Claim 2) line 16: "wherein _____, _____, _____" should read --wherein -------, ---a---, ---b--- --.

Column 10 (Claim 3) lines 25-26: "-------, is a double bond, ------- is a single bond," should read -- ---a---, is a double bond, ---b--- is a single bond, --.

Signed and Sealed this

Twenty-second Day of April 1986

[SEAL]

Attest:

DONALD J. QUIGG

Attesting Officer     Commissioner of Patents and Trademarks